United States Patent [19]

Breslow et al.

[11] Patent Number: 6,103,892
[45] Date of Patent: Aug. 15, 2000

[54] CATALYST THAT OXIDIZES STEROIDS AND OTHER SUBSTRATES WITH CATALYTIC TURNOVER

[75] Inventors: Ronald Breslow, Englewood, N.J.; Jerry Yang; Bartolo Gabriele, both of New York, N.Y.

[73] Assignee: The Trustees of Columbia University in the City of New York, New York, N.Y.

[21] Appl. No.: 09/057,417

[22] Filed: Apr. 8, 1998

[51] Int. Cl.[7] .............................. C07H 1/00; C07H 3/00; C07H 13/02
[52] U.S. Cl. ............................. 536/46; 536/103; 536/124
[58] Field of Search ................................... 536/103, 124, 536/46

[56] References Cited

PUBLICATIONS

Ellis et al. Coord. Chem. Rev. 105, 181–193, 1990.
Breslow et al. J. Am. Chem. Soc. 118: 11678–11679, 1996.
Breslow, R. "Biomimetic Control of Chemical Selectivity." *Acc. Chem. Res.* (1980) vol. 13, 170–177.
Breslow, R. "Biomimetic Chemistry and Artificial Enzymes: Catalysis by Design." *Acc. Chem. Res.* (1995)vol. 28, 146–153.
Breslow, R., Brown, A. B., McCullough, R. D. & White, P. W. "Substrate Selectivity in Epoxidation by Metalloporphyrin and Metallosalen Catalysts Carrying Binding Groups."*J. Am. Chem. Soc.* (1989) vol. 111, 4517–4518.
Breslow, R.; Gabriele, B.; Yang, J. "Geometrically Directed Selective Steroid Hydroxylation with High Turnover by a Fluorinated Artificial Cytochrome P–450." *Tetrahedron Lett.* (1998) vol. 39, 2887–2890.
Breslow, R.; Huang, Y.; Zhang, X.; Yang, J. "An artificial cytochrome P450 that hydroxylates unactivated carbons with regio– and stereoselectivity and useful catalytic turnovers." *Proc. Natl. Acad. Sci. USA* (1997)vol. 94,11156–11158.
Breslow, R.; Zhang, X.; Huang, Y. "Selective Catalytic Hydroxylation of a Steroid by an Artificial Cytochrome P–450 Enzyme." *J. Am. Chem. Soc.* (1997) vol. 119,4535–4536.
Breslow, R.; Zhang, X.; Xu, R.; Maletic, M.; Merger, R. "Selective Catalytic Oxidation of Substrates That Bind to Metalloporphyrin Enzyme Mimics Carrying Two or Four Cyclodextrin Groups and Related Matallosalens." *J. Am. Chem. Soc.* (1996) vol. 118, 11678–11679 (Exhibit 7).
Ellis, P. E.; Lyons, J. E. "Selective Air Oxidation of Light Alkanes by Activated Metalloporphyrins–The Search for a Suprabiotic System." *Coord. Chem. Rev.* (1990), vol. 105, 181–193.

Fujita, K.; Ueda, R.; Imoto, T.; Tabushi, I.; Toh, N.; Koga, T. "Guest–Induced Conformational Change of β–Cyclodextrin Capped with an Environmentally Sensitive Chromophore." *Bioorg. Chem.* (1982), vol. 11, 72–84.
Grieco, P. A. & Stuk, T. L. "Remote Oxidation of Unactivated C–H Bonds in Steroids via Oxometalloporphinates." *J. Am. Chem. Soc.* (1990) vol. 112, 7799–7801.
Groves, J. T. & Neumann, R. "Regioselective Oxidation Catalysis in Synthetic Phospholipid Vesicles. Membrane–Spanning Steroidal Metalloporphyrins." *J. Am. Chem. Soc.* (1989) vol. 111, 2900–2909 (Exhibit 11).
Groves, J. T. & Neumann, R. "Membrane–Spanning Metalloporphyrins as Site–Selective Catalysts in Synthetic Vesicles." *J. Am. Chem. Soc.* (1987) vol. 109, 5045–5047.
Groves, J. T. & Neumann, R. "Enzymic Regioselectivity in the Hydroxylation of Cholesterol Catalyzed by a Membrane–Spanning Metalloporphyrin." *J. Org. Chem.* (1988) vol. 53, 3891–3893.
Kaufman, M. D., Grieco, P. A. & Bougie, D. W. "Functionalization of Unactivated C–H Bonds in Steroids via (Salen) manganese (III) Complexes." *J. Am. Chem. Soc.* (1993) vol. 115, 11648–11649.
Stuk, T. L., Grieco, P. A. & Marsh, M. M. "Site–Selective Hydroxylation of Steroids via Oxometalloporphinates Covalently Linked to Ring D: Introduction of Hydroxyl Groups into the C(9) and C(12) Position of 5α–Androstanes." *J. Org. Chem.* (1991) vol 56, 2957–2959.

*Primary Examiner*—Gary L. Kunz
*Attorney, Agent, or Firm*—John P. White; Cooper & Dunham LLP

[57] ABSTRACT

The present invention provides a metalloporphyrin catalyst represented by the structure:

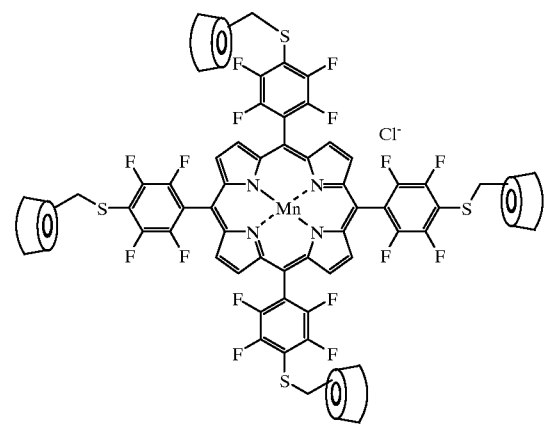

wherein ⬡ = beta-cyclodextrin

23 Claims, 5 Drawing Sheets

= beta-cyclodextrin

8

= beta-cyclodextrin

CATALYST THAT OXIDIZES STEROIDS AND OTHER SUBSTRATES WITH CATALYTIC TURNOVER

The invention disclosed herein was made with Government support under NIH Grant No. GM-18754 and NSF Grant No. CHF-94-14855. Accordingly, the U.S. Government has certain rights in this invention.

Throughout this application, various publications are referenced by author and date. Full citations for these publications may be found listed at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Enzymes are remarkably selective catalysts. They bind a particular substrate out of many available compounds in solution, then they perform a reaction at a particular position of the bound substrate (thus showing regioselectivity), often with stereoselectivity as well. The geometric control in the enzyme-substrate complex can completely dominate the normal reactivity of the substrate. For example, enzymes in the class cytochrome P450 can hydroxylate unactivated carbons in steroids while leaving much more reactive substrate positions, such as those in or next to double bonds, untouched. (Soggon, 1996; Groves & Han, 1995; Meunier, 1992--). In these enzymes an oxygen atom becomes attached to the iron atom in the metalloporphyrin, and is then transferred to the substrate within the enzyme-substrate complex.

In addition to the interest in achieving a mimic of the great rate accelerations achieved in enzymatic catalysis, imitating the selectivity is at least as important. It is critical to understand the geometric control typical of enzyme reactions in selectively functionalizing steroids and other substrates. In the earliest work, for example, a benzophenone attached to a steroid was shown to perform selective photochemical functionalization of the substrate (Breslow and Winnik, 1969; Breslow and Baldwin, 1970; Breslow and Scholl, 1971; Breslow and Kalicky, 1971; Breslow, et al, 1973; Breslow, et al, 1978; Czarniecki and Breslow, 1979; Breslow, et al., 1981). In later work, a template attached to the substrate was able to direct free radical reactions to specific carbons because of the geometry of the template-substrate species; (Breslow, 1991; Breslow, 1988; Breslow, 1980). However, there were limitations to these methods.

For one, the reagent or template was covalently attached to the substrate, so catalytic turnover was not possible. As a corollary of this, relatively simple reagents or templates were used—attached by a single flexible link—so the geometric control was limited.

The ability of oxidizing enzymes, particularly those of the cytochrome P-450 class, to perform selective hydroxylations of unactivated carbons in substrates such as steroids is of great practical importance. It also represents a great challenge for biomimetic chemistry. Indeed the phrase biomimetic chemistry was first coined in 1972 with respect to efforts to achieve selective functionalization of steroids and other hydrocarbon derivatives with use of geometric control to mimic that in enzymes.(Breslow, 1972). However, early work involved the functionalization of steroids by reagents or catalysts that were covalently attached to a steroid hydroxyl group (Breslow, 1980). Thus catalytic turnover was not possible. Furthermore, the reactions were directed photolytic insertions, or directed free radical halogenations.

In nature, the relevant enzymatic reactions involve oxidation by metalloporphyrins, with reversible enzyme binding of the substrate in such a geometry that specific substrate positions are within reach of the oxygen atom on the metal. After oxidation, the product is released, so catalytic turnover is seen.

The present invention provides for the first time a true mimic of this entire process. The present invention describes that catalytic turnover with geometric control can be used to replace currently used methods of producing various pharmaceutically important compounds. For example, it is highly desirable to replace fermentation with a clean and straight-forward chemical process. In particular, pharmaceutically important corticosteroids can be produced by such a process in place of the currently used fermentation procedures.

SUMMARY OF THE INVENTION

The present invention provides a metalloporphyrin catalyst represented by the structure:

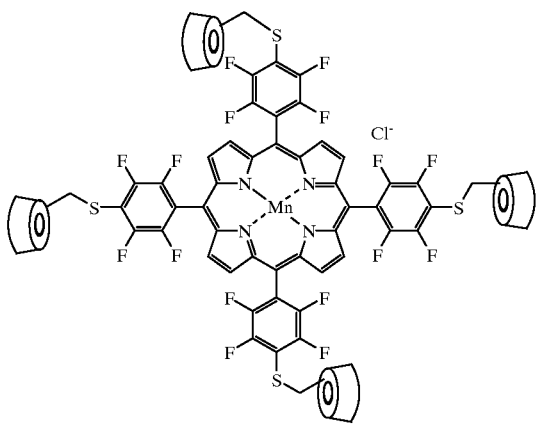

wherein 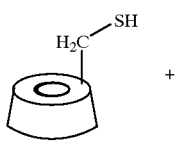 = beta-cyclodextrin

The present invention also provides a catalyst comprising a fluorophenyl metalloporphyrin having a beta cyclodextrin group on the fluorophenyl ring.

The present invention further provides a process for producing the aforementioned metalloporphoryin catalyst comprising: (a) reacting 6-deoxy-6-mercaptobetacyclodextrin,

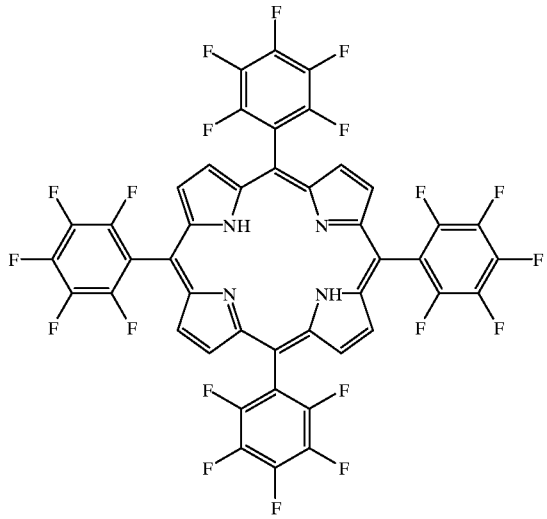

with $K_2CO_3$ to form a compound (11); and (b) reacting the compound formed in step (a) with $MnCl_2$ so as to thereby produce the catalyst (8).

Additionally, the present invention provides a method for producing a compound comprising hydroxylation of a substrate with a provided catalyst of the invention. Further, the present invention provides a method for producing a compound comprising oxidation of a substrate with the catalyst.

Finally, the present invention provides a method for producing a corticosteroid comprising hydroxylating cortexolone at the C6 position with the catalyst of the invention.

DETAILED DESCRIPTION OF THE INVENTION

Figure 1A:
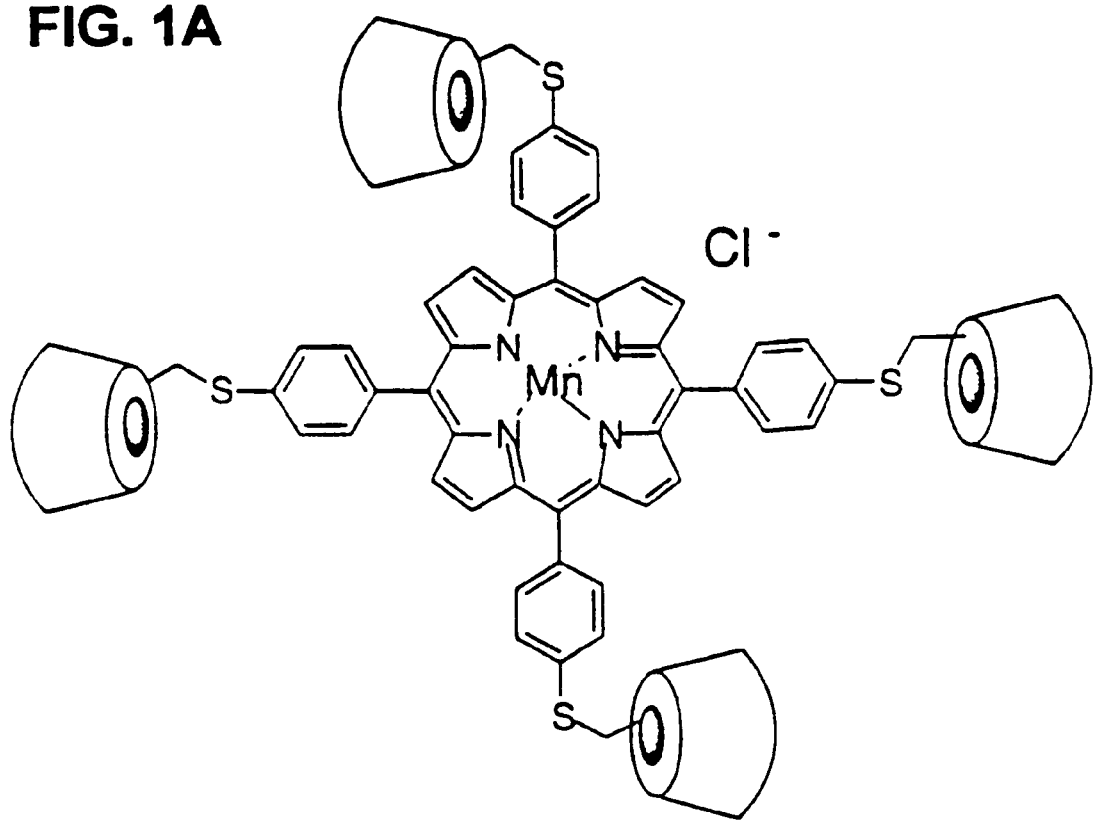
FIG. 1A. Diagramatic representation of the tetraphenyloporphyrin catalyst with Mn(III) complex capable of binding and hydroxylating substrates with two ends that bind diagonally into cyclodextrins in water so as to place a particular carbon atom directly above the Mn(III) atom.
Figure 1B:
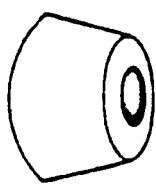
FIG. 1B. Diagramatic representation of beta-cyclodextrin.

The present invention provides a metalloporphyrin catalyst represented by the structure:

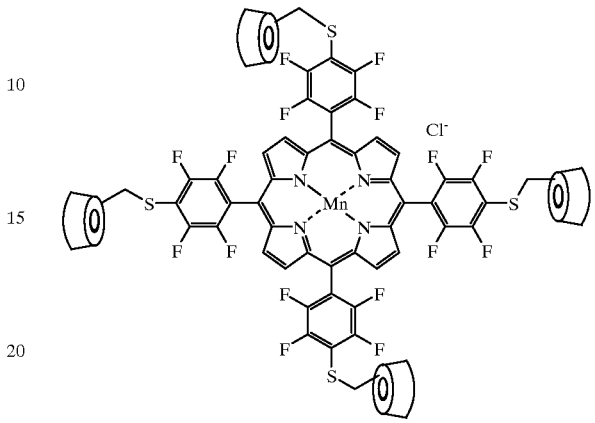

wherein 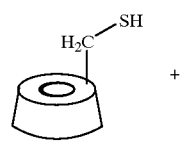 = beta-cyclodextrin

The present invention also provides a catalyst comprising a fluorophenyl metalloporphyrin having a beta cyclodextrin group on the fluorophenyl ring.

In an embodiment of this invention, the metalloporphyrin is a transition metal metalloporphyrin, such as manganese, iron, chromium, cobalt, nickel, ruthenium or osmium metalloporphyrin. In an embodiment of this invention, the fluorophenyl metalloporphyrin is a fluorotetraphenyl metalloporphyrin, such as a tetrafluorotetraphenyl metalloporphyrin. In an embodiment of the present invention, the beta-cyclodextrin group is linked to the fluorophenyl by a sulphur, carbon, nitrogen, oxygen or phosphorous bond which may be in a para, meta or ortho orientation. In an embodiment of this invention, the phenyl rings are attached at the meso positions of the porphyrin. In one embodiment of the present invention, the catalyst is capable of geometric selectivity. In an embodiment of the present invention, the catalyst is capable of selective hydroxylation of a substrate. In another embodiment of the present invention, the catalyst is capable of selective oxidation of a substrate. In one embodiment of this invention, the geometric selectivity is for the formation of the 6α-hydroxy derivative of androstanediol. In another embodiment the betacyclodextrin group is an alphacyclodextrin group or a gammacyclodextrin group.

The present invention further provides a process for producing the above-mentioned metalloporphoryin catalyst comprising: (a) reacting 6-deoxy-6-mercaptobetacyclodextrin, -continued

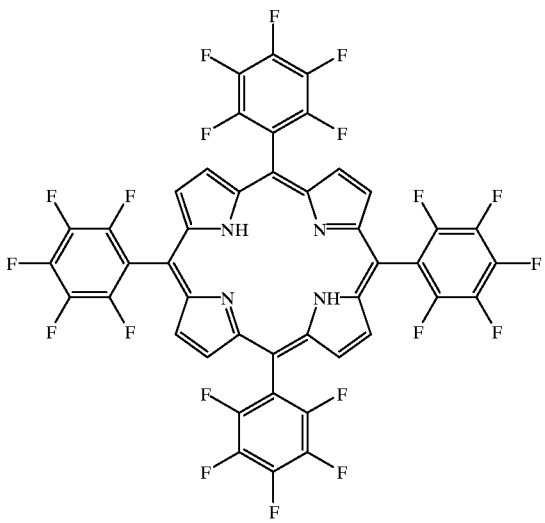

with $K_2CO_3$ to form a compound (11); and (b) reacting the compound formed in step (a) with $MnCl_2$ so as to thereby produce the catalyst (8).

In an embodiment of this invention step (a) further comprises performing the reaction in dry DMF. In another embodiment of this invention step (a) further comprises performing the reaction at room temperature. In yet another embodiment of this invention step (a) further comprises performing the reaction in the dark.

Additionally, the present invention provides a method for producing a compound comprising hydroxylation of a substrate with the catalyst. Further, the present invention provides a method for producing a compound comprising oxidation of a substrate with the catalyst.

In an embodiment of this invention, the substrate is a terpene, a terpenoid or a terpenoid derivative. In an embodiment of this invention, the substrate is a steroid, steroid derivative, steroid precursor, steroid derivative precursor or steroid degradation product. In an embodiment of this invention, the substrate is vitamin A, vitamin D, β carotene, androstanediol, dihydrocholestanol, lithocholic acid, lithocholenic acid, coprostanol, cortexolone, 11-desoxycorticosterone, lanosterol or an ester derivative of any of the foregoing.

Finally, the present invention provides a method for producing a corticosteroid comprising hydroxylating cortexolone at the C6 position with the catalyst.

As used herein, the term, "stereoselective" refers to a selection of an optical isomer. "Diastereomer" refers to the optical isomer of a compound whose molecule contains more than one asymmetric atom and does not exhibit a mirror image relationship. "Enantiomer" is an optical isomer which exhibits the mirror image relationship. An asymmetric carbon atom is a carbon atom in union with four dissimilar atoms or groups. Compounds containing asymmetric carbon atoms are capable of existing in two optically active forms which are distinguished by being respectively levorotatory (L-form) or dextrorotatory (D-form) and also in some cases being enantiomeric. Thus, enantiomers are mirror image isomers; diastereomers are non-mirror image isomers. Molecules that are not superimposable on their mirror images are chiral. Chirality is necessary and sufficient for the existence of enantiomers. A compound whose molecules are achiral (without chirality) cannot exist as enantiomers. A racemic mixture is one in which there is a mixture of the D-form and L-form of the compound. The term optically active refers to isomers whose properties differ only in the direction or rotation of polarized light. Optical activity results from chirality: the non-superimposability of certain molecules on their mirror images. Optical activity is evident when a mixture contains an excess of one enantiomer, whereby an excess of the net optical rotation can be detected.

As used herein, the term "regioselective" refers to the selective production of branched as opposed to linear molecules. "Enantioselectivity" represents the maximal asymmetric induction and minimal racemization of the optically active products.

As used herein, the term "geometric control" refers to a substrate-catalyst complex having a specific spatial orientation wherein reactivity is directed to a particular spatial position in the complex. Thus, the geometry within the substrate-catalyst complex determines the product formed.

As used herein, the term "turnover" refers to the relative number of molecules of substrate converted into products per number of molecules of catalyst prior to the exhaustion of a given reaction.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Geometrically Directed Selective Steroid Hydroxylation with High Turnover by a Fluorinated Artificial Cytochrome P-450

Groves and Neumann (Groves, J. T. & Neumann, R. (1989) J. Am. Chem. Soc. 111, 2900–2909; Groves, J. T. & Neumann, R. (1987) J. Am. Chem. Soc. 109, 5045–5047; Groves, J. T. & Neumann, R. (1988) J. Org. Chem. 53, 3891–3893) have shown that organization in a bilayer can be used to achieve hydroxylation of a steroid by a metalloporphyrin catalyst, but catalytic turnover was blocked by strong binding of the product. Grieco and colleagues (Grieco, P. A. & Stuk, T. L. (1990) J. Am. Chem. Soc. 112, 7799–7801; Kaufman, M. D., Grieco, P. A. & Bougie, D. W. (1993) J. Am. Chem. Soc. 115, 11648–11649; Stuk, T. L., Grieco, P. A. & Marsh, M. M. (1991) J. Org. Chem. 56, 2957–2959;) have also shown that a metalloporphyrin can hydroxylate a steroid in an intramolecular reaction if it is covalently attached, but again, this is not a catalytic process with turnover. The catalyst of the present invention indeed binds a substrate, performs a hydroxylation catalyzed by a metalloporphyrin, and then releases the product to perform true turnover catalysis. In one example, the hydroxylation is highly selective for an otherwise unreactive and unremarkable steroid position. The geometry within the complex of substrate with artificial enzyme determines the product formed.

To achieve turnover catalysis—and thus to justify the use of a more complex catalyst, with more than one binding interaction to a substrate so as to improve selectivity, metalloporphyrin derivatives (as in the cytochrome P450 enzymes) and metallosalens carrying substrate binding groups were examined. In one study (Breslow, R., Brown, A. B., McCullough, R. D. & White, P. W. (1989) J. Am. Chem. Soc. 111, 4517–4518), metal binding groups were attached to the porphyrin or salen system, so that substrates carrying metal binding groups at both ends could coordinate to the catalysts through bridging metal ions. When two such coordinations occurred, to stretch the substrate across the central metal ion of the metalloporphyrin or metallosalen, a substrate double bond was catalytically epoxidized with turnover.

This was extended to substrates that do not coordinate to metal ions. Synthesized metallosalens carrying two beta-cyclodextrin groups, and metalloporphyrins carrying two and four beta-cyclodextrin groups (Breslow, R., Zhang, X., Xu, R., Maletic, M. & Merger, R. (1996) J. Am. Chem. Soc. 118, 11678–11679; Breslow, R., Zhang, X. & Huang, Y. (1997) J. Am. Chem. Soc. 119, 4535–4536) were synthesized. In water the porphyrins were able to bind olefins having hydrophobic end groups, and catalyze selective double bond epoxidation (Breslow, R., Zhang, X., Xu, R., Maletic, M. & Merger, R. (1996) J. Am. Chem. Soc. 118, 11678–11679). The salens bound the substrates but did not catalyze the epoxidations, apparently because the geometry of the catalysts changes greatly when they go to the metallo-oxo intermediate structures. (Breslow, R, et al PNAS 94: 1115–58 (1997)

Figure 2:
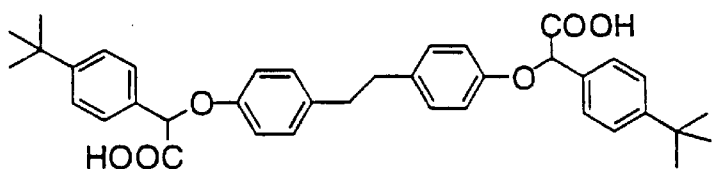
FIG. 2. Diagramatic representation of Dihydrostilbene
Figure 3:
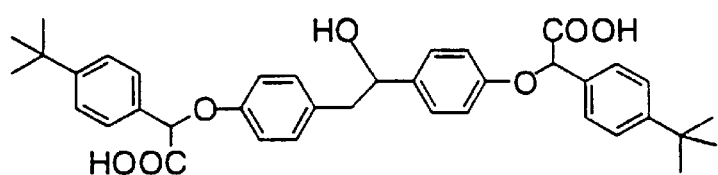
FIG. 3. Diagramatic representation of the product of dihydrostilbene hydroxylated by the catalyst of FIG. 1 with iodosobenzene as oxidant.

Subsequent work (Breslow, R., Zhang, X. & Huang, Y. (1997) J. Am. Chem. Soc. 119, 4535–4536) showed that the porphyrin catalyst 1 (FIG. 1A) that carries four beta-cyclodextrin units and a bound Mn (III) was able to catalyze the hydroxylation of bound substrates in water. The diphenylethane derivative 2 (FIG. 2) was hydroxylated completely to form product 3 (FIG. 3) with 7 mol % of catalyst 1 (FIG. 1A) using iodosobenzene as the oxidant, so there were at least 15 turnovers. The iodosobenzene transfers an oxygen atom to the Mn(III), and the resulting metallo-oxo species hydroxylates a nearby carbon of the bound substrate.

Control reactions excluded alternative mechanisms, such as free radical chain processes. The hydroxylation was dependent on the presence of the two hydrophobic tert-butylphenyl groups at each end of 2 (FIG. 2), that bound into two beta-cyclodextrin units trans to each other in catalyst 1 (FIG. 1A). The binding constant for substrate 2 (FIG. 2) into the porphyrin precursor of 1 (FIG. 1A), lacking the bound Mn(III), was $(1.3\pm0.2)\times10^5$ M$^{-1}$, determined by titration calorimetry. Two molecules of 2 (FIG. 2) were bound, presumably on each face of the porphyrin. In the hydroxylation reactions, pyridine was added to coordinate to one face of the metalloporphyrin so as to direct substrate and the oxygen atom to the other face.

Figure 5:
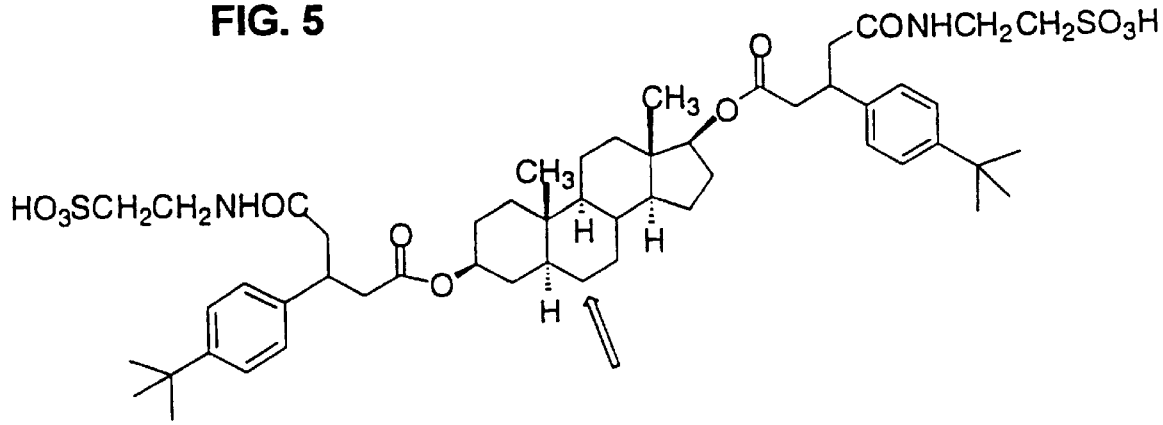
FIG. 5. Diagramatic representation of derivative of androstanediol.
Figure 6:
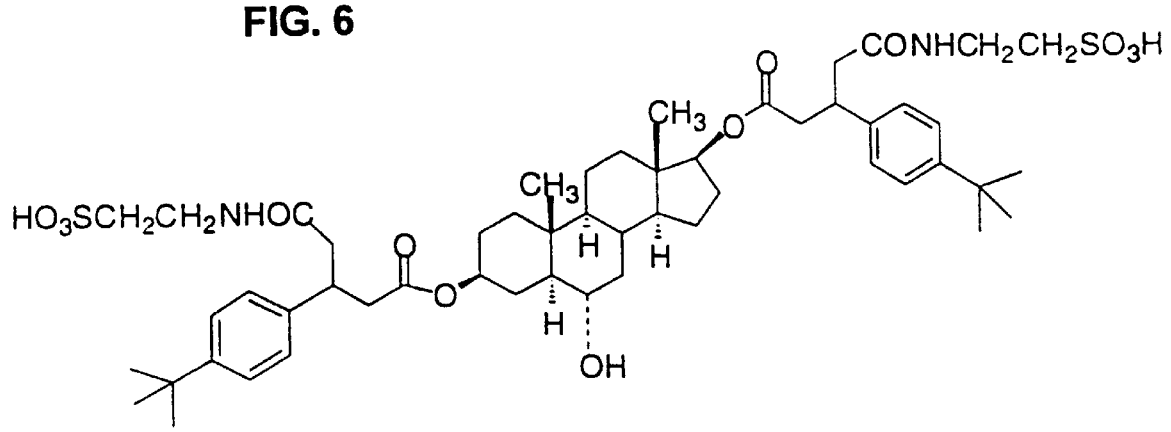
FIG. 6. Diagramatic representation of the product of hydroxylation of the androstanediol derivative of FIG. 5 by the catalyst of FIG. 1A with iodosobenzene as oxidant, which was produced with complete selectivity for the formation of the 6α hydroxy derivative.

Androstane-3,17-diol 4 (FIG. 4) was converted to the diester 5 (FIG. 5), with tert-butylphenyl hydrophobic binding groups and solubilizing sulfonate groups. Molecular models indicated that the two tert-butylphenyl groups can bind into cyclodextrins on the opposite side of 1 (FIG. 1A) so as to put ring B of the steroid directly over the metalloporphyrin unit. With 10 mol % of catalyst 1 (FIG. 1A), and an excess of iodosobenzene, substrate 5 (FIG. 5) was converted to the 6-hydroxy derivative 6 (FIG. 6). After ester hydrolysis the only products were 7 (FIG. 7) (40%) and recovered starting material 4 (FIG. 4) (60%), so four turnovers had been achieved. No other product could be detected. The structure of triol 7 (FIG. 7) was established by NMR spectroscopy and comparison with an authentic sample. Thus the regiochemistry and stereochemistry of this reaction appears to be complete, within experimental limits.

By contrast, a derivative of cholestanol with only one attached hydrophobic binding group, whose binding geometry is therefore less well defined, gave several hydroxylated products with the same catalyst 1 (Breslow, R., Zhang, X. & Huang, Y. (1997) J. Am. Chem. Soc. 119, 4535–4536). An analog of 5 (FIG. 5) lacking the tert-butylphenyl groups was not hydroxylated.

Figure 7:
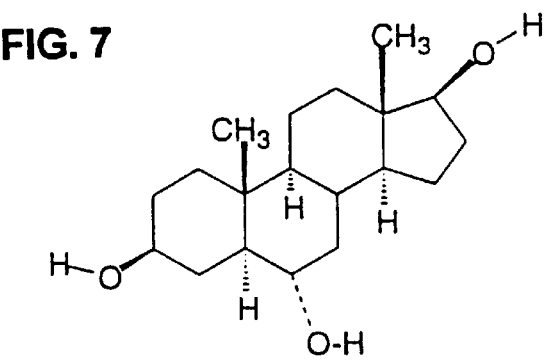
FIG. 7. Diagramatic representation of androstantriol, produced by hydrolyzing the product of FIG. 6 by the catalyst of FIG. 1A with iodosobenzene as oxidant.
Figure 9:
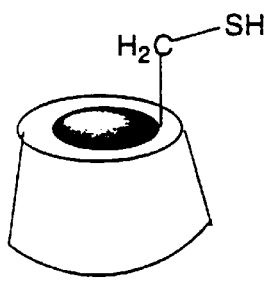
FIG. 9. Diagramatic representation of 6-deoxy-6-mercaptobetacyclodextrin.
Figure 10:
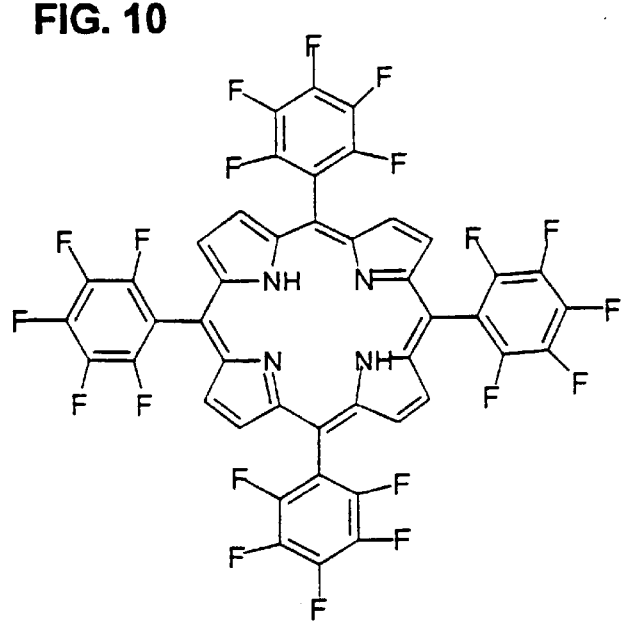
FIG. 10. Diagramatic representation of pentafluorophenyl porphyrin derivative.

The ability of enzymes such as the cytochrome P-450 group to perform chemical reactions independent of the intrinsic reactivity of the substrate is a challenge for biomimetic chemistry. For example, in the biosynthesis of cholesterol such enzymes oxidize methyl groups on saturated carbons in the presence of carbon-carbon double bonds that are not attacked. This is the result of the geometry of the enzyme-substrate complex, that holds the substrate next to an iron atom in a porphyrin ring of the enzyme. The synthesis of a tetraphenylporphyrin derivative whose Mn(III) complex 1 can bind and hydroxylate substrates with two ends that bind diagonally into cyclodextrins in water so as to place a particular carbon atom directly above the Mn(III) atom was described (Breslow et al., 1996; Breslow, et al., 1997a; Breslow, et al., 1997b). With iodosobenzene as oxidant a catalyst 1 (FIG. 1A) was able to achieve the hydroxylation of a dihydrostilbene 2 (FIG. 2) to product 3 (FIG. 3)(Breslow, et al, 1996) with 650 turnovers, (Breslow, et al., 1997b) and also to hydroxylate the derivative 5 (FIG. 5) of androstanediol 4 (FIG. 4) with complete selectivity for the formation of the 6α hydroxy derivative 6 (FIG. 6), hydrolyzed to androstantriol 7 (FIG. 7). This selective hydroxylation is directed by the geometry of the catalyst-substrate complex, as in the enzyme. However, the hydroxylation of 5 (FIG. 5) proceeded with only 3–5 turnovers before the catalyst 1 (FIG. 1A) was oxidatively destroyed. (Ellis and Lyons, 1990). It seemed likely that the oxidative destruction of the catalyst involved the porphyrin system of 1 (FIG. 1A), not the cyclodextrins, and if so prior work indicated how to solve the problem. Tetraphenylporphyrin based catalysts are much more stable with pentafluorophenyl rings, which decrease the oxidizability of the porphyrin meso positions that carry the phenyl groups. (Fujita, et al., 1982). The catalyst of the present invention has now been synthesized 8 (FIG. 8A), with tetrafluorophenyl rings. The synthesis was straight forward. Reaction of 6-deoxy-6-mercapto-betacyclodextrin 9 (FIG. 9) (Lindey, et al., 1987) and the pentafluorophenyl porphyrin derivative 10 (FIG. 10) (Fitzpatrick and Siggia, 1973) with $K_2CO_3$ in dry DMF at RT in the dark afforded dark red porphyrin 11 (FIG. 11) exhibited a 95% yield. The compound showed the expected $^1H$ and $^{19}F$ NMR spectra, and in particular the $^{19}F$ NMR spectrum indicated that the four p-fluorines of 10 (FIG. 10) had been replaced. The UV-vis spectrum of 11 was typical of a porphyrin, with λmax 412, 510, 582 nm. With $MnCl_2$ compound 11 (FIG. 11) was converted in 93% yield to catalyst 8 (FIG. 8A), with LD-MS 5582 (M$^+$) and λmax 369, 458, 554 nm.

Figure 4:
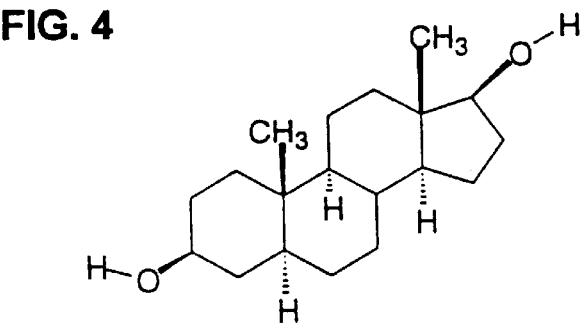
FIG. 4. Diagramatic representation of androstanediol.
Figure 8A:
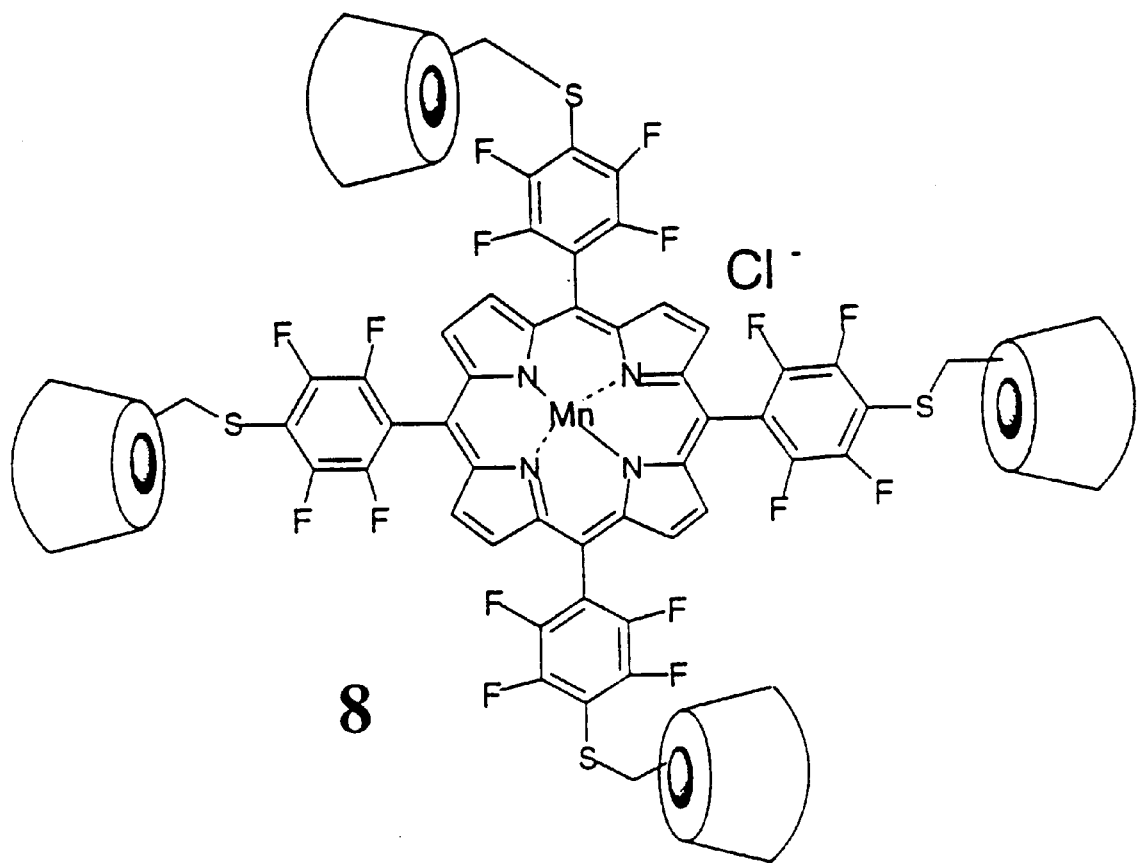
FIG. 8A. Diagramatic representation of tetraphenylporphyrin catalyst with tetrafluorophenyl rings.

Substrate 5 (FIG. 5) was oxidized at RT in neutral water with 10 equivalents of PhIO and 10 equivalents of pyridine using varying concentrations of 5 (FIG. 5) and of catalyst 8 (FIG. 8A). The products were assayed by hydrolysis to starting androstanediol 4 (FIG. 4) and to androstanetriol 7 (FIG. 7), again the only product, followed by benzoylation and quantitative high pressure liquid chromatography (HPLC) analysis. Under the conditions used, the benzoylation is known to be quantitative and reliable for such an hplc assay. (Fillion, et al., 1991). The assays were run in triplicate, and the errors were ca. 0.5%. With 1.46 mM 5 (FIG. 5) and 0.0146 mM 8 (FIG. 8A) (1 mol %), followed by hydrolysis, the 6α hydroxy derivative 7 (FIG. 7) was formed in 95% yield, indicating 95 turnovers. With the use of 1.02 mM 5 (FIG. 5) and 0.00102 mM 8 (FIG. 8A) (0.1 mol %) the product 7 (FIG. 7) was found in 18.7% yield, along with recovered starting androstanediol 4 (FIG. 4). Thus there were 187 turnovers. The lower number of turnovers with high conversion presumably reflects some product inhibition. (Breslow, et al., 1997).

These results indicate that with the stabilized fluorocatalyst 8 (FIG. 8A) both high conversion and high turnover in the selective hydroxylation of 5 (FIG. 5) to 6 (FIG. 6) can be achieved. As the geometry of such complexes is varied, other selective hydroxylations of interest may be achieved, mimicking the selectivities achieved by the enzymes of the cytochrome P-450 group.

Discussion

Enzymes generally bind their substrate and then use the action of two or more well-placed functional groups to achieve catalysis. This scheme leads to substrate selectivity, reaction selectivity, and stereo-selectivity. Binding can be achieved by metal coordination, ion pairing, Lewis acid-base coordination, or hydrogen bonding in nonaqueous solvents, and by metal or Lewis acid-base coordination or hydrophobic interaction in water solution. Simple metal coordination has been used to hold a substrate next to catalytic group. Cyclodextrins bind hydrophobic substrates in water solution. Various functional groups can be attached to the cyclodextrins, and the cavity can also be modified.

An instructive series of studies examined the acylation of cyclodextrin hydroxyl groups by bound substrate. This is not a catalytic reaction, but it mimics the first step in the hydrolysis of esters and peptides by serine proteases. Bender had seen a ca. 100-fold acceleration of the deacylation of m-nitro-phenyl acetate when it reacts with β-cyclodextrin, compared with hydrolysis under the same conditions. Model building indicated that the substrate could bind well into the cyclodextrin cavity, but that forming the tetrahedral intermediate during acylation caused the aromatic ring to pull up partly out the cavity.

A series of ferrocene esters was prepared that bound into the cyclodextrin activity and acylated it with as much as a 5 900 000-fold acceleration relative to hydrolysis, and with good chiral selectivity as well. Model building and physical studies indicated that the tetrahedral intermediated, and transition states that resemble it, can retain almost all of their original binding geometry.

Studies on this system showed that the rigid binding of derivatives was useful with good leaving such as ρ-nitrophenoxide ion, but a problem with poorer leaving groups. Conversion of a tetrahedral intermediated to the acylated product requires a rotation that is blocked by excessive rigidity in the complex; by introducing an extra degree of freedom we solve the problem. The message is that for catalysis one needs good binding of the transition state, not just the substrate, and enough flexibility must be retained to permit along the reaction path.

Binding into simple cyclodextrin was enough to direct a selective aromatic substitution reaction in which a chlorine atom is delivered to the bound substrate by one of the cyclodextrin hydroxyl groups. The selectivity was greater than that for an enzyme that catalyzes the same reaction. Furthermore, cyclodextrins can bind two substrate together, catalyzing the Diels-Alder reaction for instance. This is a reaction for which there are no natural enzyme catalysts, illustrating the use of biomimetic chemistry to go beyond the range of biochemical catalysis.

Some of the most interesting enzymatic processes involve the selective oxidation of unactivated positions in substrates, directed by the geometry of the enzyme-substrate complex. For example, heme-containing enzymes can selectively hydroxylate unactivated methyl groups while leaving double bonds of a substrate untouched. A mimic of such regioselectivity could be of great use in chemical synthesis.

Early work on this problem started with a process termed "remote oxidation", in which a photoactive benzophenone unit was covalently attached to a steroid or a flexible chain. Irradiation led to functionalization of the substrate dictated by geometric proximity as in the enzymes. Such reactions were made catalytic by the use of substrate-attached templates that bound chlorine atoms and directed them to geometrically accessible positions on a steroid or other substrate. Of course such an attached template acts as a catalyst only in the formal sense; it can be recovered at the end of the reaction, but must be used in stoichiometric amounts. True turnover catalysis was not achieved in this early work.

Geometric control of the functionalization of flexible substrate is limited by their conformational randomness; double binding of a catalyst or reagent to both ends of the chain is useful. Benzophenone functionalization of a flexible chain can be made selective with binding of each chain end by ion pairing or hydrogen bonding, and double metal-ion coordination was used to immobilized a flexible chain on a metal porphyrin catalyst that performed double-bond epoxidation and also on a related metallosalen system. Metallosalens have been prepared with two attached cyclodextrin groups, and related porphyrin oxidizing system 22) that perform double hydrophobic binding of appropriate substrate. Fluorinated phenyl rings provide stability to oxidative degradation.

Geometric control leads to useful selectivity, even in the functionalization of otherwise inreactive substrates. The present invention provides a catalyst with geometric control and selective rapid catalytic reactions with good turnover.

Thus, the present invention, described herein above, provides for the first time a true mimic of catalytic process.

Catalytic turnover with geometric control can be used to replace currently used methods of producing various pharmaceutically important compounds. For example, it is highly desirable to replace fermentation with a clean and straight-forward chemical process. In particular, pharmaceutically important corticosteroids can be produced by such a process in place of the currently used fermentation procedures.

EXPERIMENTAL PROCEDURES

The hydroxylation of 2 (FIG. 2) by catalyst 1 (FIG. 1A) was complete is 45 minutes at room temperature. The hydroxylation of 5 (FIG. 5) by catalyst 8 (FIG. 8A) was allowed to proceed for 4 hours; addition of an additional 10 equivalents of oxidant and a further 2 hours standing did not increase the substrate conversion, indicating that catalyst lifetime is the limiting factor.

Figure 11:
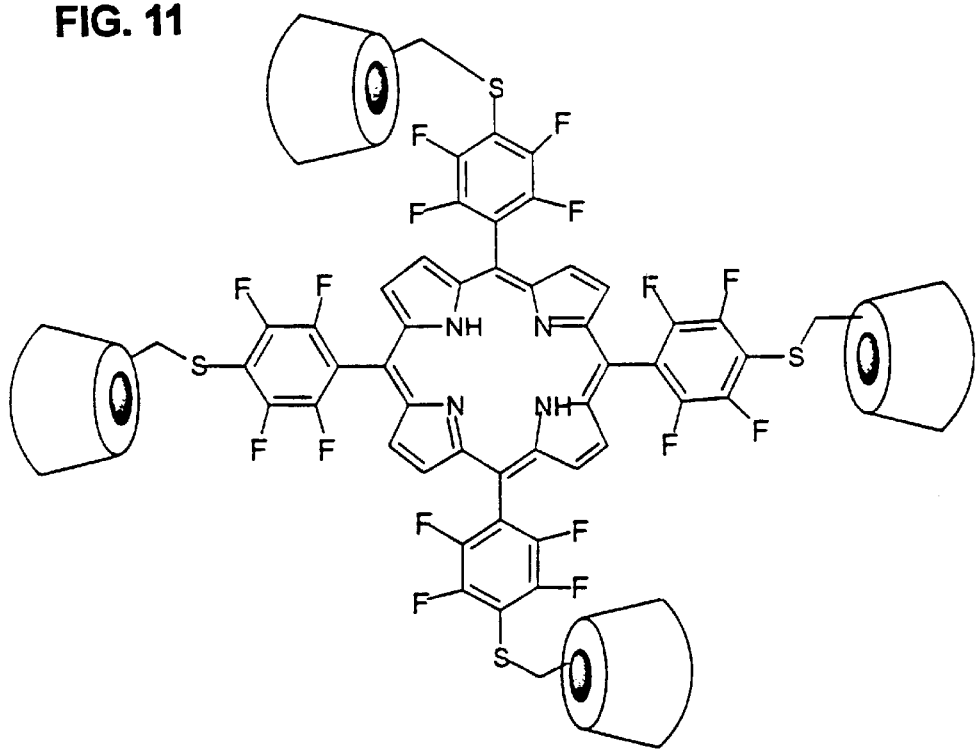
FIG. 11. Diagramatic representation of dark red porphyrin produced from the pentafluorophenyl porphyrin derivative of FIG. 10 and $K_2CO_3$ in dry DMF at room temperature in the dark.

Preparation of T[(β-CDCH$_2$SF$_4$)P]P (FIG. 11)

A 50 mL round bottom flask with side-arm was charged with 5,10,15,20-tetrakis(pentaflurophenyl)-21H,23H-porphine (50 mg, 0.051 mmol; commercially available from Aldrich), dry DMF (5 mL) and K$_2$CO$_3$ (71 mg, 0.514 mmol) in this order under argon. After stirring 5 minutes, 6-deoxy-6-mercapto-β-cyclodextrin (293 mg. 0.255 mmol) (Fujita, K., et al. Bioorg. Chem. 1982, 11 72) was added under argon and the mixture was stirred for 24 hours at room temperature. DMF was removed in vacuo and the residue was precipitated in acetone. The dark red precipitate was filtered, washed with acetone and dried under vacuum overnight. The crude product was purified by gel filtration (Sephadex G-75, 20–50μ) with water as eluent to obtain, after lyophilization, 266 mg of T[(β-CDCH$_2$SF$_4$)P]P as a dark red power–95% yield). This preparation was carried out shielding the reaction flask from the external light. UV-vis (H$_2$O): λ$_{max}$=412, 510,582 nm. $^1$H NMR (400 MHz; d$_6$-DMSO:D$_2$O=95:5 AT 80° C.). δ-9.22 (s, 8 H β-pyrrole protons), 5.09-4.78 [m, 28 H, C(1)H], 4.23-4.12 [m, 4 H, C(5)h-CH$_2$-S-porphyrin], 3.95-3.10 {m, 244 H, C(2)H+C(3)H+C(4)H+C(5)H+C(6)H+C(2)OH+C(3)OH+C(6)OH on cyclodextrins], 31 3.13 (2 H, 2 NH) $^{19}$F NMR (372 MHz, $d_6$-DMSO:$D_2O$=95:5 at 353 K): (−132.88)–(133.32) (m, 8 F on aromatic rings), (−138.03) (m, 8 F on aromatic rings).

Figure 8B:
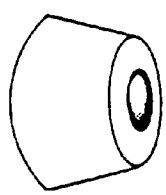
FIG. 8B. Diagramatic representation of beta-cyclodextrin.

Preparation of Mn{T[(β-CDCH$_2$SF$_4$)P]P}Cl (FIG. 8)

A mixture of T[(β-CDCH$_2$SF$_4$)P]P (203 mg, 0.037 mmol), MnCl$_2$ (93 mg, 0.739 mmol), 2,6-lutidine (120 mg, 1.12 mmol) and dry DMF (20 mL) was refluxed with stirring for 4.5 hours. The solution was concentrated to about 5 mL by rotary evaporation, then acetone (30 mL) was added under stirring to obtain a dark red precipitate, which was filtered, washed with acetone and dried under vacuum overnight. The crude product was purified by gel filtration (Sephadex G-75, 20–50μ) with water as eluent to obtain, after lyophilization, 192 mg of Mn{T[(β-CDCH$_2$SF$_4$)P]P}Cl as a dark red power (93% yield). This preparation was carried out shielding the reaction flask from the external light. UV-vis (H$_2$O): $\lambda_{max}$=369,458,554 nm. LD-MS (matrix with α-cyano-4-hydroxycinnamic acid, performed by Schering-Plough)m/z=5570–5615 (calculated: 5582).

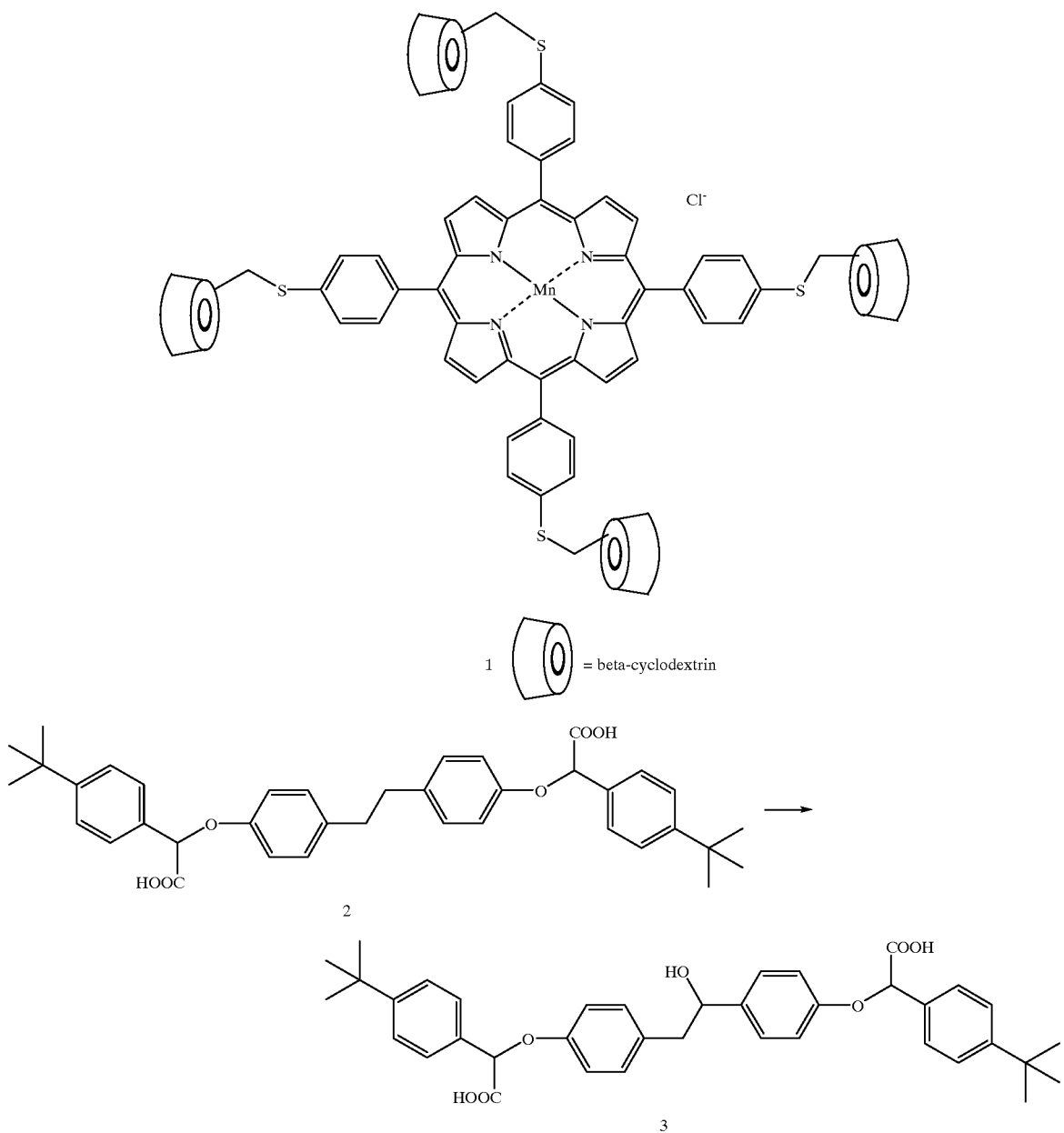

-continued
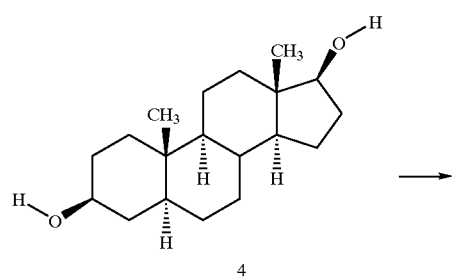
4
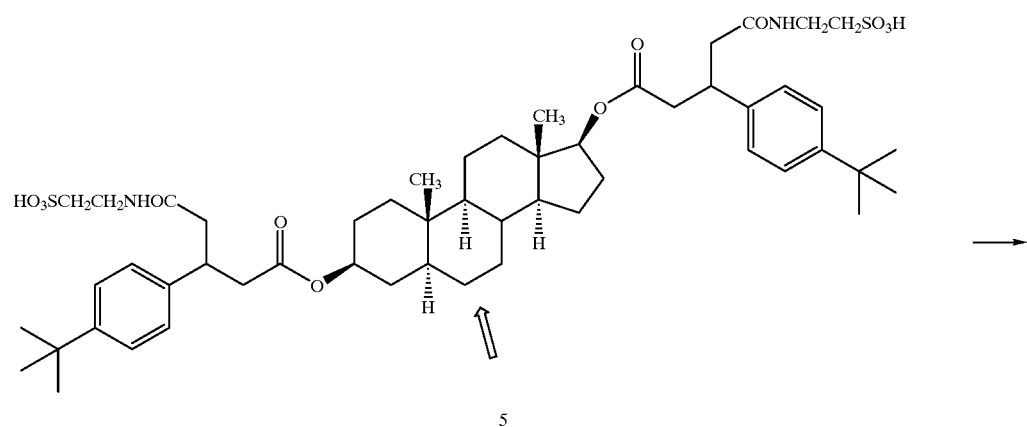
5
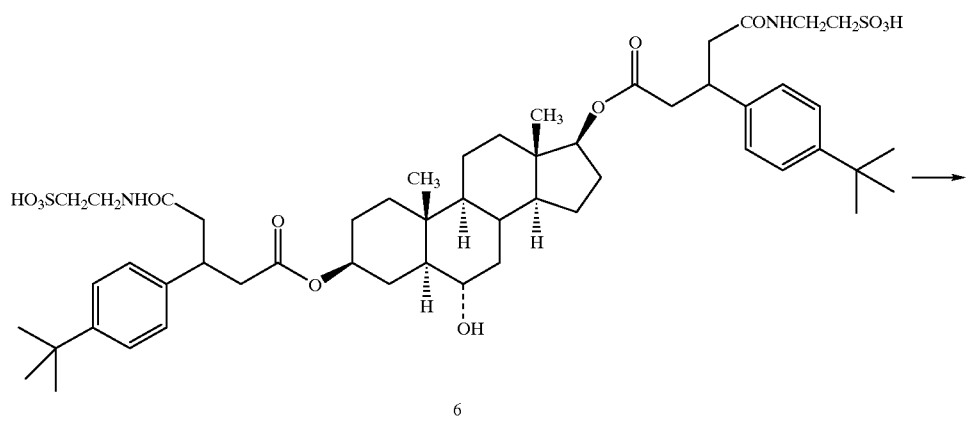
6
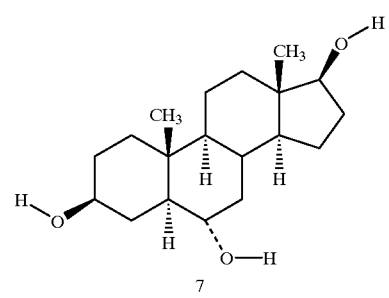
7

-continued
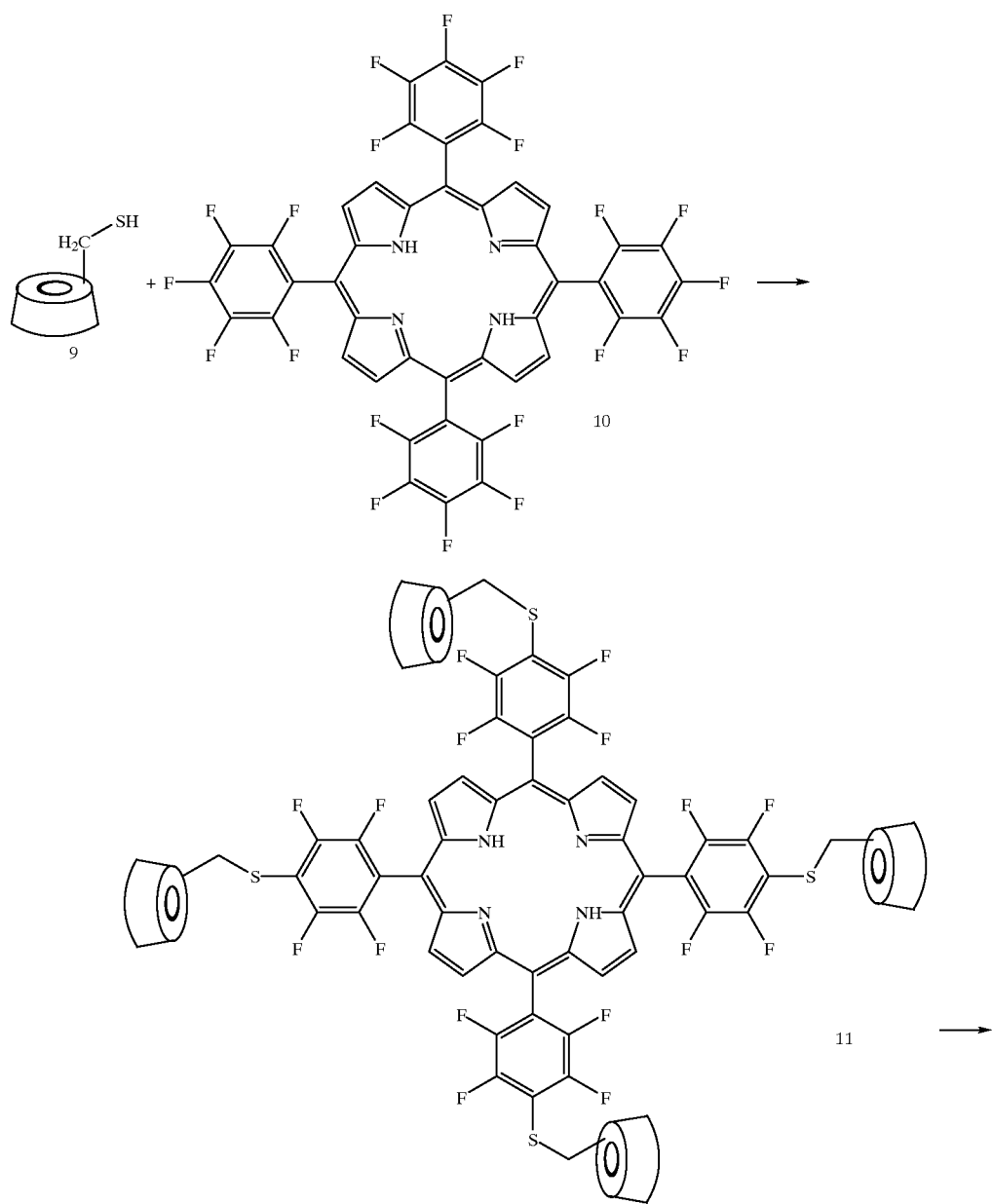

-continued

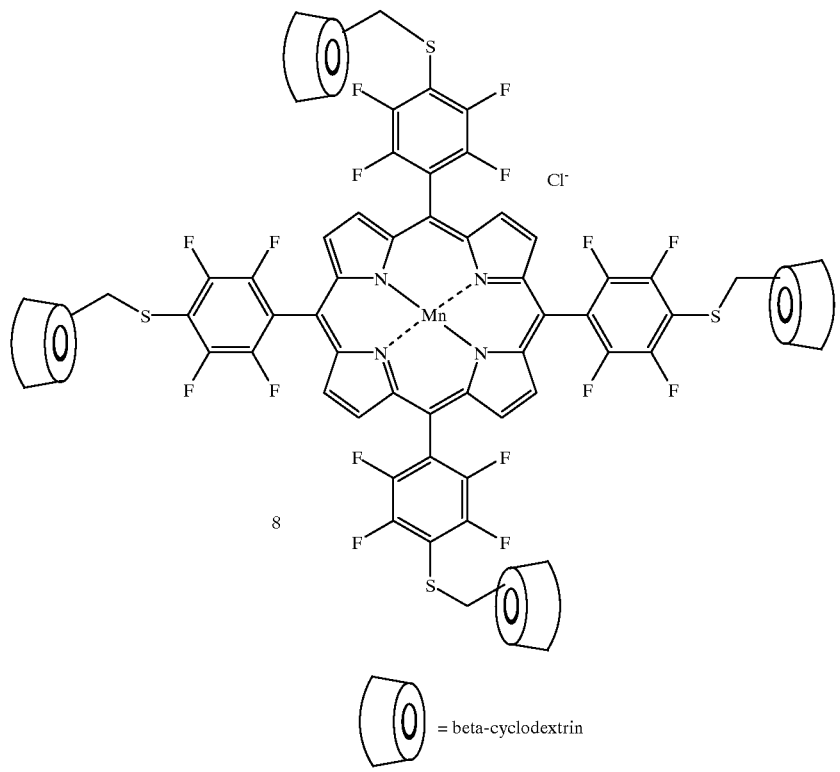

REFERENCES

Breslow, R.; Zhang, X.; Xu, R.; Maletic, M.; Merger, R. *J. Am. Chem. Soc.* 1996, 118, 11678.

Breslow, R.; Zhang, X.; Huang, Y. *J. Am. Chem. Soc.* 1997, 119, 4535.

Breslow, R.; Huang, Y.; Zhang, X.; Yang, J. *Proc. Natl. Acad. Sci. USA* 1997, 94, 11156.

Ellis, P. E.; Lyons, J. E. *Coord. Chem. Rev.* 1990, 105, 181–193.

Fujita, K.; Ueda, T.; Imoto, T.; Tabushi, I.; Toh, N.; Koga, T. *Bioorg. Chem.* 1982, 11, 72.

Lindsey, J. S.; Schreiman, I. C.; Hsu, H. C.; Kearney, P. C. Marguerettaz, A. M. *J. Org. Chem.* 1987, 52, 827.

Fitzpatrick, F.; Siggia, S. *Anal. Chem.* 1973, 45, 2310–2314.

Fillion, L.; Lee, J.; Gosselin, C. *J. Chromatography* 1991, 547, 105–112.

Woggon, W. D. (1996) Cytochrome P 450: Significance, Reaction Mechanisms and Active Site Analogues, ed. Smidtchen, F. P. (Springer, Berlin), pp. 39–96.

Groves, J. T. & Han, Y.-Z (1995) Models and Mechanism of Cytochrome P-450 Action, ed. Ortiz de Montellano, P. R. (Plenum, New York), pp. 3–48.

Meunier, B. (1992) Chem. Rev. 92, 1411–1456.

Breslow, R. & Winnik, M. A. (1969) J. Am. Chem. Soc. 91, 3083–3084.

Breslow, R. Baldwin, S. W. (1970) J. Am. Chem. Soc. 92, 732–734.

Breslow, R. & Scholl, P. C. (1971) J. Am. Chem. Soc. 93, 2331–2333.

Breslow, R. & Kalicky, P. (1971) J. Am. Chem. Soc. 93, 3540–3541.

Brelsow, R., Baldwin, S., Flechtner, T., Kalicky, P., Liu, S. & Washburn, W. (1973) J. Am. Chem. Soc. 95, 3251–3262.

Breslow, R., Rothbard, J., Herman, F. & Rodriguez, M. L. (1978) J. Am. Chem. Soc. 100, 1213–1218.

Czarniecki, M. F. & Breslow, R. (1979) J. Am. Chem. Soc. 101, 3675–3676.

Breslow, R., Rajagopalan, R. & Schwartz, J. (1981) J. Am. Chem. Soc. 103, 2905–2907.

Breslow, R. (1991) in Oxidation by Remote Functionalization Methods, ed. Trost, B. M. (Pergamon, Oxford), Vol. 7, pp. 39–52.

Breslow, R. (1988) Chemtracts Org. Chem. 1, 333–348.

Breslow, R. (1980) Acc. Shem. Res. 13, 170–177.

Groves, J. T. & Neumann, R. (1989) J. Am. Chem. Soc. 111, 2900–2909.

Groves, J. T. & Neumann, R. (1987) J. Am. Chem. Soc. 109, 5045–5047.

Groves, J. T. & Neumann, R. (1988) J. Org. Chem. 53, 3891–3893.

Grieco, P. A. & Stuk, T. L. (1990) J. Am. Chem. Soc.. 112, 7799–7801.

Kaufman, M. D., Grieco, P. A. & Bougie, D. W. (1993) J. Am. Chem. Soc. 115, 11648–11649.

Stuk, T. L., Grieco, P. A. & Marsh, M. M. (1991) J. Org. Chem. 56, 2957–2959.

Breslow, R., Brown, A. B., McCullough, R. D. & White, P. W. (1989) J. Am. Chem. Soc. 111, 4517–4518.

Breslow, R., Zhang, X. & Huang, Y. (1997) J. Am. Chem. Soc. 119, 4535–4536.

McCarthy, M.-B. & White, R. E. (1983) J. Biol. Chem. 258, 9153–9158.

What is claimed is:

1. A metalloporphyrin catalyst represented by the structure:

[structure of Mn-metalloporphyrin with four pentafluorophenyl groups each bearing a thio-beta-cyclodextrin substituent, with Cl⁻ counterion]

wherein [symbol] = beta-cyclodextrin

2. A catalyst comprising a fluorophenyl metalloporphyrin having a beta cyclodextrin group on the fluorophenyl ring.

3. The catalyst of claim 2, wherein the metalloporphyrin is a transition metal metalloporphyrin.

4. The catalyst of claim 2, wherein the metalloporphyrin is a manganese, iron, chromium, cobalt, nickel, ruthenium or osmium metalloporphyrin.

5. The catalyst of claim 2, wherein the fluorophenyl metalloporphyrin is a fluorotetraphenyl metalloporphyrin.

6. The catalyst of claim 2, wherein the fluorophenyl metalloporphyrin is a tetrafluorotetraphenyl metalloporphyrin.

7. The catalyst of claim 2, wherein the beta cyclodextrin group is linked to the fluorophenyl by a sulfur, carbon, nitrogen, oxygen or phosphorous bond.

8. The catalyst of claim 7, wherein the bond is in a para, meta or ortho orientation.

9. The catalyst of claim 7, wherein the phenyl rings are attached at the meso positions of the porphyrin.

10. The catalyst of claim 2, wherein the catalyst exhibits geometric selectivity.

11. The catalyst of claim 2, wherein the catalyst exhibits selective hydroxylation of a substance.

12. The catalyst of claim 2, wherein the catalyst exhibits selective oxidation of a substance.

13. The catalyst of claim 10, wherein the geometric selectivity is for the formation of the 6α-hydroxy derivative of androstanediol.

14. A process for producing the metalloporphoryin catalyst of claim 1 comprising:

(a) reacting 6-deoxy-6-mercaptobetacyclodextrin,

[structure of mercapto-beta-cyclodextrin] + [structure of pentafluorophenyl-substituted free-base porphyrin]

With K₂CO₃ to form a compound; and (b) reacting the compound formed in step (a) with MnCl₂ so as to thereby produce catalyst; and (c) recovering the catalyst so produced.

15. The process of claim 14, wherein step (a) further comprises performing the reaction in dry dimethylformamide.

16. The process of claim 14, wherein step (a) further comprises performing the reaction at room temperature.

17. The process of claim 14, wherein step (a) further comprises performing the reaction in the dark.

18. A method for producing a compound comprising hydroxylation of a substrate with the catalyst of claim 1.

19. A method for producing a compound comprising oxidation of a substrate with the catalyst of claim 1.

20. The method of claim 18 or 19, wherein the substrate is a terpene, or a terpenoid.

21. The method of claim 18 or 19, wherein the substrate is a steroid.

22. The method of claim 18 or 19, wherein the substrate is vitamin A, vitamin D, β-carotene, androstandiol, dihydrocholestanol, lithocholic acid, lithocholenic acid, coprostenol, cortexolone, 11-desoxycorticosterone, lanosterol or an ester derivative of any of the foregoing.

23. A method for producing a corticosteroid comprising hydroxylating cortexolone at the C6 position with the catalyst of claim 1.

* * * * *